US010820795B1

(12) United States Patent
Weise et al.

(10) Patent No.: US 10,820,795 B1
(45) Date of Patent: Nov. 3, 2020

(54) METHOD AND DEVICE FOR IMPROVED INTERPUPILLARY DISTANCE MEASUREMENT

(71) Applicant: Apple Inc., Cupertino, CA (US)

(72) Inventors: Thibaut Weise, Menlo Park, CA (US); Justin D. Stoyles, San Francisco, CA (US); Michael Kuhn, Los Gatos, CA (US); Reinhard Klapfer, San Francisco, CA (US); Stefan Misslinger, San Jose, CA (US)

(73) Assignee: APPLE INC., Cupertino, CA (US)

( * ) Notice: Subject to any disclaimer, the term of this patent is extended or adjusted under 35 U.S.C. 154(b) by 147 days.

(21) Appl. No.: 16/015,683

(22) Filed: Jun. 22, 2018

Related U.S. Application Data

(60) Provisional application No. 62/564,881, filed on Sep. 28, 2017.

(51) Int. Cl.
*A61B 3/11* (2006.01)
*G02C 13/00* (2006.01)
*G02B 27/01* (2006.01)
*G06K 9/20* (2006.01)
*G02B 7/02* (2006.01)

(52) U.S. Cl.
CPC .......... *A61B 3/111* (2013.01); *G02B 27/0101* (2013.01); *G02C 13/003* (2013.01); *G06K 9/209* (2013.01); *G02B 7/02* (2013.01)

(58) Field of Classification Search
CPC ........ G06T 19/006; G06F 3/011; G06F 3/012; G06F 3/013; G06F 3/014; H04N 13/327; H04N 13/344
See application file for complete search history.

(56) References Cited

U.S. PATENT DOCUMENTS

| 2012/0162764 A1* | 6/2012 | Shimizu | H04N 13/327 359/473 |
|---|---|---|---|
| 2013/0318776 A1* | 12/2013 | Jacobs | G02B 27/01 29/592.1 |
| 2013/0321925 A1* | 12/2013 | Jacobs | G02B 27/017 359/630 |
| 2013/0322683 A1* | 12/2013 | Jacobs | G02B 27/0149 382/103 |
| 2014/0274391 A1* | 9/2014 | Stafford | H04N 13/327 463/32 |
| 2016/0065952 A1* | 3/2016 | Han | G06K 9/00604 345/8 |
| 2016/0091720 A1* | 3/2016 | Stafford | G02B 27/0093 345/8 |
| 2016/0131902 A1* | 5/2016 | Ambrus | G02B 27/0093 345/156 |
| 2016/0349837 A1* | 12/2016 | Miller | G06F 3/012 |
| 2016/0353093 A1* | 12/2016 | Lyon | G02B 27/017 |
| 2017/0099481 A1* | 4/2017 | Held | G02B 27/017 |

* cited by examiner

Primary Examiner — Jeffery A Brier
(74) Attorney, Agent, or Firm — Fernando & Partners, LLP

(57) ABSTRACT

In one implementation, a method includes: determining an interpupillary distance (IPD) measurement for a user based on a function of depth data obtained by the depth sensor and image data obtained by the image sensor; and calibrating a head-mounted device (HMD) provided to deliver augmented reality/virtual reality (AR/VR) content by setting one or more presentation parameters of the HMD based on the IPD measurement in order to tailor one or more AR/VR displays of the HMD to a field-of-view of the user.

26 Claims, 9 Drawing Sheets

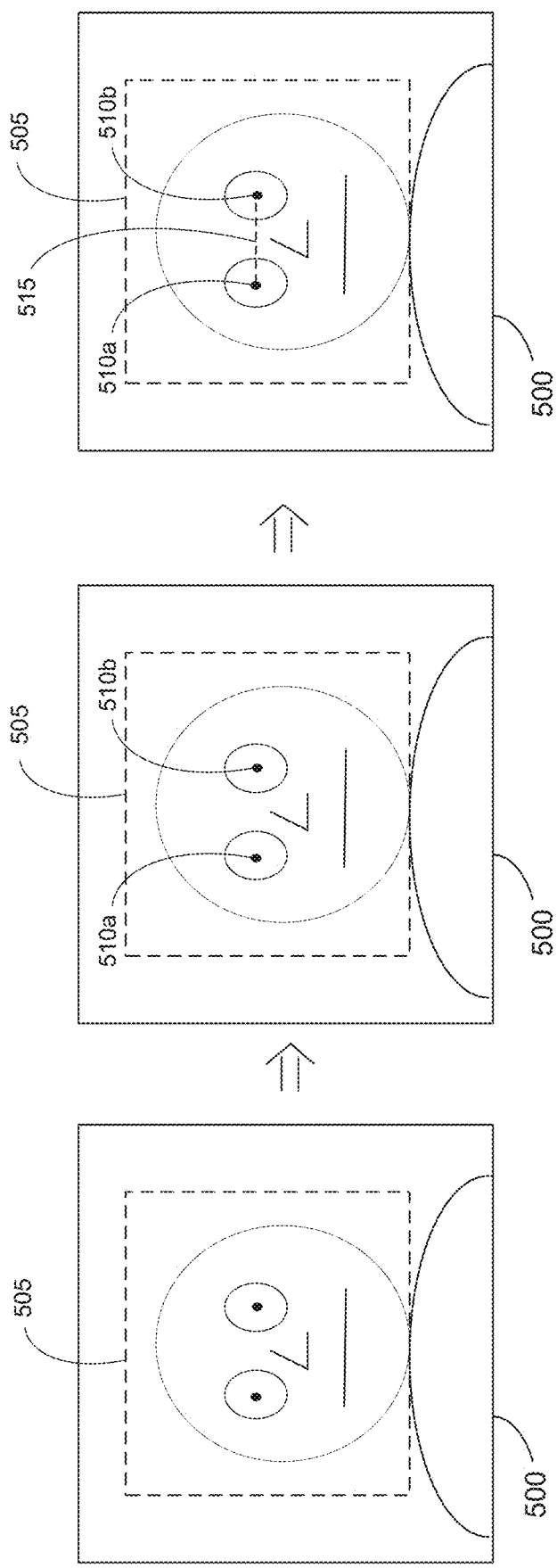

METHOD AND DEVICE FOR IMPROVED INTERPUPILLARY DISTANCE MEASUREMENT

CROSS-REFERENCE TO RELATED APPLICATIONS

This application claims priority from U.S. Provisional Patent App. No. 62/564,881, filed on Sep. 28, 2017, hereby incorporated by reference in its entirety.

TECHNICAL FIELD

The present disclosure generally relates to augmented reality/virtual reality (AR/VR) content consumption, and in particular, to systems, methods, and devices for calibrating a head-mounted device (HMD) for improved AR/VR content delivery.

BACKGROUND

Virtual reality (VR), augmented reality (AR), and mixed reality (MR) are becoming more popular due to their remarkable ability to alter a user's perception of the world. For example, VR, AR, and MR are used for learning purposes, gaming purposes, content creation purposes, social media and interaction purposes, or the like. These technologies differ in the user's perception of his/her presence. VR transposes the user into a virtual space so their VR perception is different from his/her real-world perception. In contrast, AR takes the user's real-world perception and adds something to it. MR is a combination of VR and AR.

These technologies are becoming more commonplace due to, for example, miniaturization of hardware components, improvements to hardware performance, and improvements to software efficiency. As one example, a user may experience VR content by using a head-mounted device (HMD) that encloses the user's field-of-view and is tethered to a computer. As another example, a user may experience AR content by wearing an HMD that still allows the user to see his/her surroundings (e.g., glasses with optical see-through).

In the above examples, the HMD is typically a one-size-fits-all device. However, users of the HMD have anatomical differences (e.g., head circumference, interpupillary distance (IPD), etc.) that impact the VR experience among users when wearing one of these devices. For example, content may be displayed out of focus or off center for one user as compared to another user due to differences in the IPD between the two users.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIGS. 5A-5B illustrate example image data in accordance with some implementations.

Figure 1:
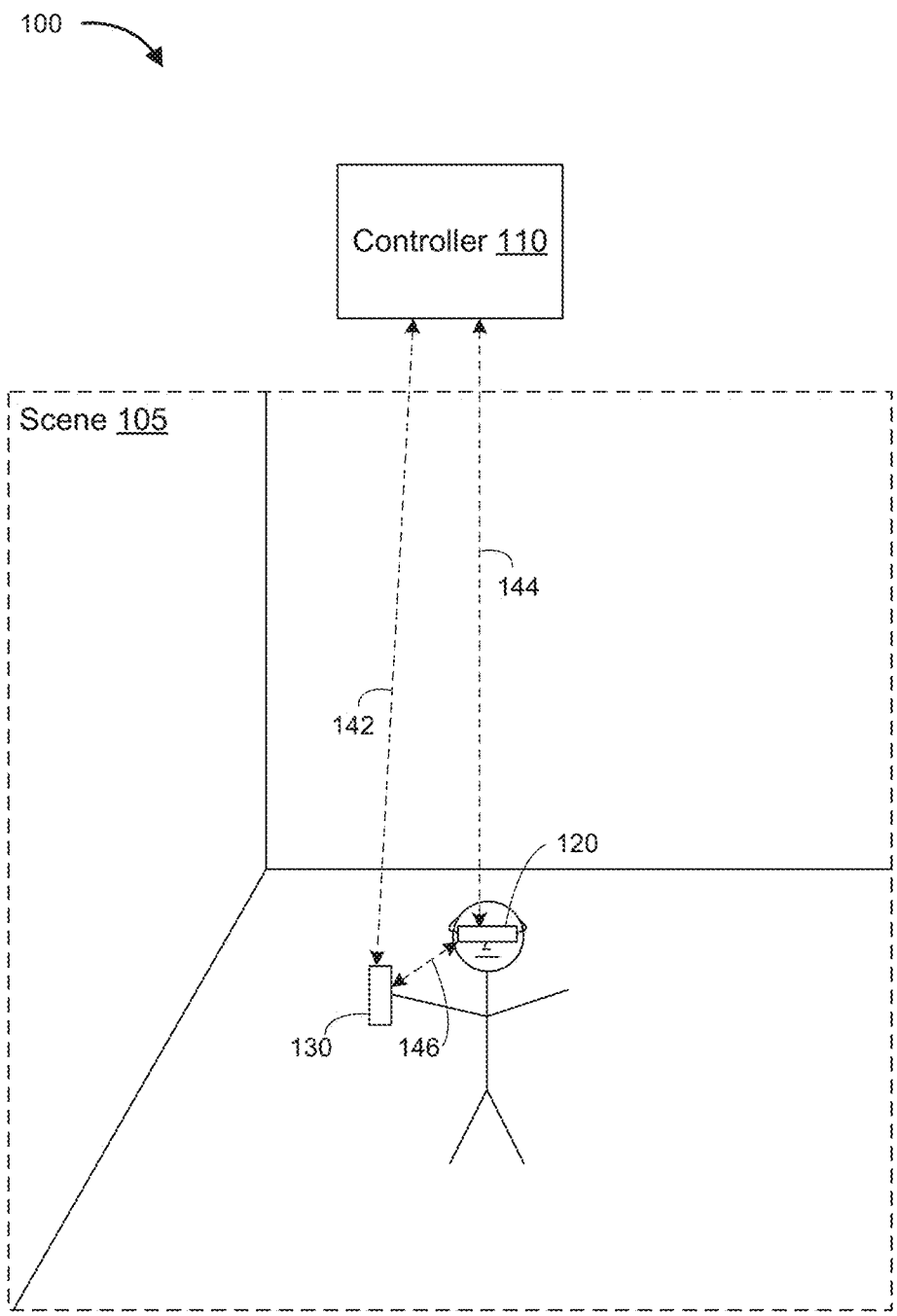
FIG. 1 is a block diagram of an example operating environment in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for calibrating a head-mounted device (HMD) for improved augmented reality/virtual reality (AR/VR) content delivery. According to some implementations, the method is performed at a device with one or more processors, non-transitory memory, an image sensor, and a depth sensor. The method also includes: determining an interpupillary distance (IPD) measurement for a user based on a function of depth data obtained by the depth sensor and image data obtained by the image sensor; and calibrating a head-mounted device (HMD) provided to deliver augmented reality/virtual reality (AR/VR) content by setting one or more presentation parameters of the HMD based on the IPD measurement in order to tailor one or more AR/VR displays of the HMD to a field-of-view of the user.

In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein. In accordance with some implementations, a non-transitory computer readable storage medium has stored therein instructions, which, when executed by one or more processors of a device, cause the device to perform or cause performance of any of the methods described herein. In accordance with some implementations, a device includes: one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices and circuits have not been described in exhaustive detail so as not to obscure more pertinent aspects of the example implementations described herein.

According to some implementations, a user may experience VR using an HMD that encloses the user's field-of-view and is tethered to a computer. In this example, a typical HMD is one-size-fits-all. However, users have physiological differences (e.g., head size, IPD, etc.) that impact the VR experience from user-to-user when wearing one of these one-size-fits-all HMDs. For example, content may be displayed out of focus or off center for one user as compared to another user due to differences in the IPD between the two users. Therefore, the below described innovation calibrates the HMD by setting one or more presentation parameters (e.g., hardware and/or software parameters) of the HMD based on an IPD measurement of the user in order to tailor the AR/VR experience to a field-of-view of the user. In some implementations, the IPD measurement of the user is determined based on both image data and depth data that characterizes the user of the HMD.

FIG. 1 is a block diagram of an example operating environment 100 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 100 includes a controller 110, a head-mounted device (HMD) 120, and an optional calibration device 130.

In some implementations, the controller 110 is configured to manage and coordinate an augmented reality/virtual reality (AR/VR) experience for the user. In some implementations, the controller 110 includes a suitable combination of software, firmware, and/or hardware. The controller 110 is described in greater detail below with respect to FIG. 2. In some implementations, the controller 110 is a computing device that is local or remote relative to the scene 105. For example, the controller 110 is a local server located within the scene 105. In another example, the controller 110 is a remote server located outside of the scene 105 (e.g., a cloud server, central server, etc.).

In some implementations, the controller 110 is communicatively coupled with the HMD 120 via one or more wired or wireless communication channels 144 (e.g., BLUETOOTH, IEEE 802.11x, IEEE 802.16x, IEEE 802.3x, etc.). In some implementations, the controller 110 is communicatively coupled with the calibration device 130 via one or more wired or wireless communication channels 142 (e.g., BLUETOOTH, IEEE 802.11x, IEEE 802.16x, IEEE 802.3x, etc.). In some implementations, the HMD 120 is communicatively coupled with the calibration device 130 via one or more wired or wireless communication channels 146 (e.g., BLUETOOTH, IEEE 802.11x, IEEE 802.16x, IEEE 802.3x, etc.).

In some implementations, the HMD 120 is configured to present the AR/VR experience to the user. In some implementations, the HMD 120 includes a suitable combination of software, firmware, and/or hardware. The HMD 120 is described in greater detail below with respect to FIG. 3. In some implementations, the functionalities of the controller 110 are provided by and/or combined with the HMD 120.

According to some implementations, the HMD 120 presents an augmented reality/virtual reality (AR/VR) experience to the user while the user is virtually and/or physically present within the scene 105. In some implementations, while presenting an augmented reality (AR) experience, the HMD 120 is configured to present AR content and to enable optical see-through of the scene 105. In some implementations, while presenting a virtual reality (VR) experience, the HMD 120 is configured to present VR content.

In some implementations, the user wears the HMD 120 on his/her head. As such, the HMD 120 includes one or more AR/VR displays provided to display the AR/VR content. For example, the HMD 120 encloses the field-of-view of the user. In some implementations, the HMD 120 is replaced with an AR/VR chamber, enclosure, or room configured to present AR/VR content in which the user does not wear the HMD 120.

In some implementations, the calibration device 130 is configured to optionally determine an interpupillary distance (IPD) measurement for the user. In some implementations, the calibration device 130 is configured to optionally calibrate one or more presentation parameters of the HMD 120 based on the IPD measurement for the user in order to tailor the one or more AR/VR displays of the HMD 120 to a field-of-view of the user. In some implementations, the HMD 120 is configured to auto-calibrate its one or more presentation parameters by determining the IPD measurement.

In some implementations, the calibration device 130 corresponds to a computing device such as a webcam, desktop computer, kiosk, set-top box, over-the-top box, gaming console, laptop computer, tablet, mobile phone, wearable computing device, or the like. In some implementations, the calibration device 130 includes a suitable combination of software, firmware, and/or hardware. The calibration device 130 is described in greater detail below with respect to FIG. 4.

Figure 2:
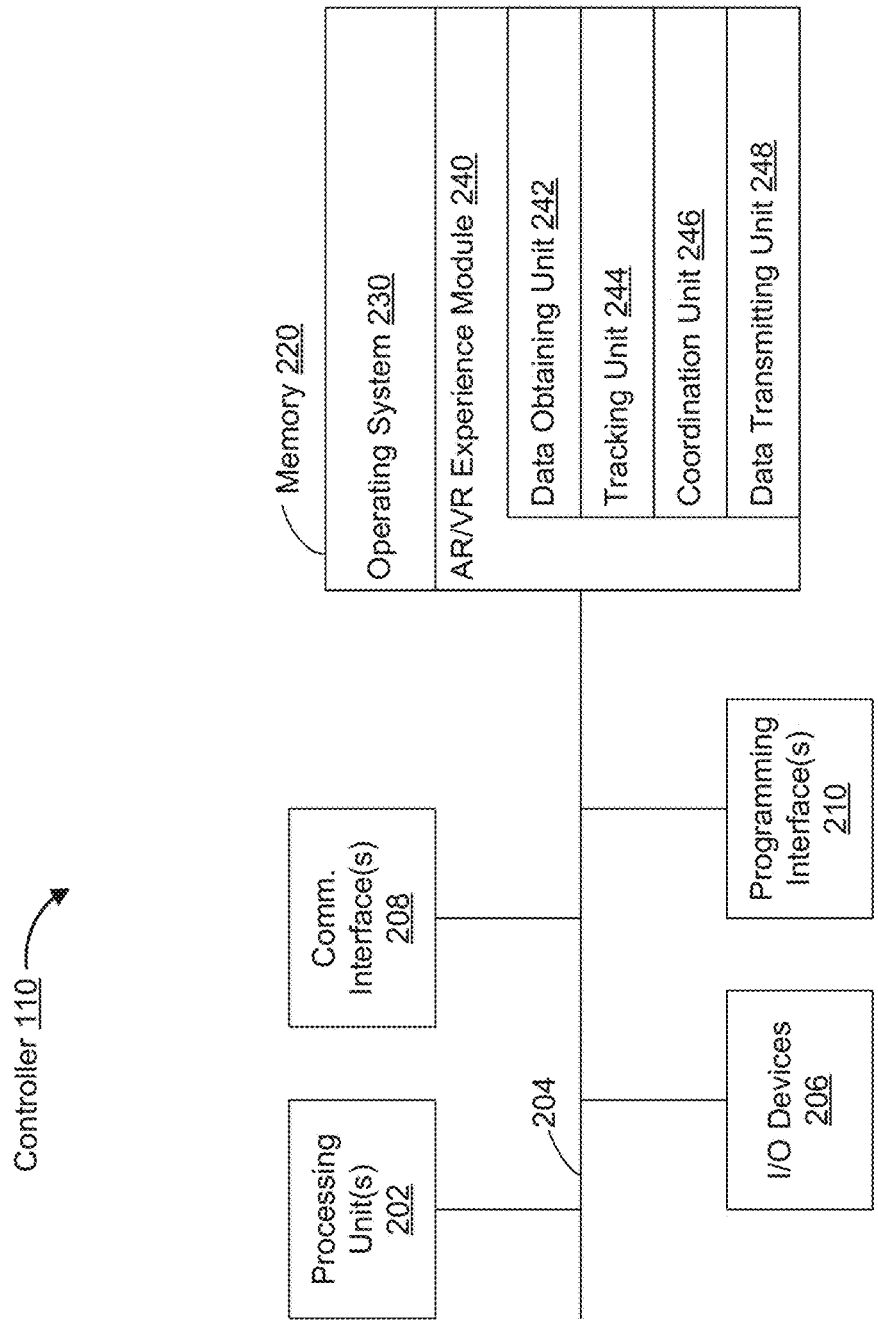
FIG. 2 is a block diagram of an example controller in accordance with some implementations.

FIG. 2 is a block diagram of an example of the controller 110 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations, the controller 110 includes one or more processing units 202 (e.g., microprocessors, application-specific integrated-circuits (ASICs), field-programmable gate arrays (FPGAs), graphics processing units (GPUs), central processing units (CPUs), processing cores, and/or the like), one or more input/output (I/O) devices 206, one or more communication interfaces 208 (e.g., universal serial bus (USB), FIREWIRE, THUNDERBOLT, IEEE 802.3x, IEEE 802.11x, IEEE 802.16x, global system for mobile communications (GSM), code division multiple access (CDMA), time division multiple access (TDMA), global positioning system (GPS), infrared (IR), BLUETOOTH, ZIGBEE, and/or the like type interface), one or more programming (e.g., I/O) interfaces 210, a memory 220, and one or more communication buses 204 for interconnecting these and various other components.

In some implementations, the one or more communication buses 204 include circuitry that interconnects and controls communications between system components. In some implementations, the one or more I/O devices 206 include at least one of a keyboard, a mouse, a touchpad, a joystick, one or more microphones, one or more speakers, one or more image sensors, one or more displays, and/or the like.

The memory 220 includes high-speed random-access memory, such as dynamic random-access memory (DRAM), static random-access memory (SRAM), double-data-rate random-access memory (DDR RAM), or other random-access solid-state memory devices. In some implementations, the memory 220 includes non-volatile memory, such as one or more magnetic disk storage devices, optical disk storage devices, flash memory devices, or other non-volatile solid-state storage devices. The memory 220 optionally includes one or more storage devices remotely located from the one or more processing units 202. The memory 220 comprises a non-transitory computer readable storage medium. In some implementations, the memory 220 or the non-transitory computer readable storage medium of the memory 220 stores the following programs, modules and data structures, or a subset thereof including an optional operating system 230 and an augmented reality/virtual reality (AR/VR) experience module 240.

The operating system 230 includes procedures for handling various basic system services and for performing hardware dependent tasks. In some implementations, the AR/VR experience module 240 is configured to manage and coordinate one or more AR/VR experiences for one or more users (e.g., a single AR/VR experience for one or more users, or multiple AR/VR experiences for respective groups of one or more users). To that end, in various implementations, the AR/VR experience module 240 includes a data obtaining unit 242, a tracking unit 244, a coordination unit 246, and a data transmitting unit 248.

In some implementations, the data obtaining unit 242 is configured to obtain data (e.g., presentation data, user interaction data, sensor data, location data, etc.) from at least one of the HMD 120 and the calibration device 130. To that end, in various implementations, the data obtaining unit 242 includes instructions and/or logic therefor, and heuristics and metadata therefor.

In some implementations, the tracking unit 244 is configured to map the scene 105 and to track the position/location of at least one of the HMD 120 and the calibration device 130 with respect to the scene 105. To that end, in various implementations, the tracking unit 244 includes instructions and/or logic therefor, and heuristics and metadata therefor.

In some implementations, the coordination unit 246 is configured to manage and coordinate the AR/VR experience presented to the user by the HMD 120. To that end, in various implementations, the coordination unit 246 includes instructions and/or logic therefor, and heuristics and metadata therefor.

In some implementations, the data transmitting unit 248 is configured to transmit data (e.g., presentation data, location data, etc.) to at least one of the HMD 120 and the calibration device 130. To that end, in various implementations, the data transmitting unit 248 includes instructions and/or logic therefor, and heuristics and metadata therefor.

Although the data obtaining unit 242, the tracking unit 244, the coordination unit 246, and the data transmitting unit 248 are shown as residing on a single device (e.g., the controller 110), it should be understood that in other implementations, any combination of the data obtaining unit 242, the tracking unit 244, the coordination unit 246, and the data transmitting unit 248 may be located in separate computing devices.

Moreover, FIG. 2 is intended more as a functional description of the various features which are present in a particular embodiment as opposed to a structural schematic of the implementations described herein. As recognized by those of ordinary skill in the art, items shown separately could be combined and some items could be separated. For example, some functional modules shown separately in FIG. 2 could be implemented in a single module and the various functions of single functional blocks could be implemented by one or more functional blocks in various implementations. The actual number of modules and the division of particular functions and how features are allocated among them will vary from one embodiment to another and, in some implementations, depends in part on the particular combination of hardware, software, and/or firmware chosen for a particular embodiment.

Figure 3:
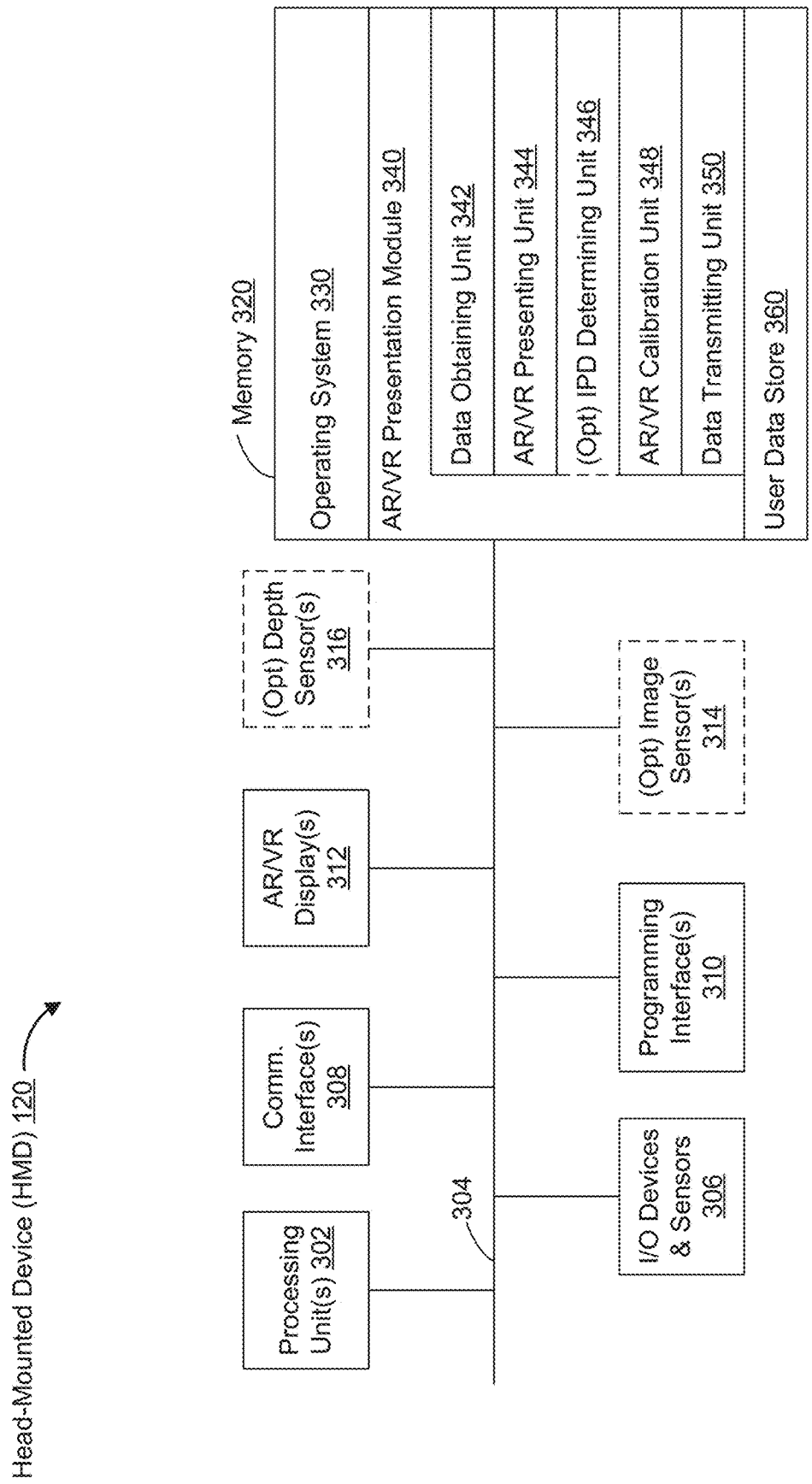
FIG. 3 is a block diagram of an example head-mounted device (HMD) in accordance with some implementations.

FIG. 3 is a block diagram of an example of the head-mounted device (HMD) 120 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations, the HMD 120 includes one or more processing units 302 (e.g., microprocessors, ASICs, FPGAs, GPUs, CPUs, processing cores, and/or the like), one or more input/output (I/O) devices and sensors 306, one or more communication interfaces 308 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, and/or the like type interface), one or more programming (e.g., I/O) interfaces 310, one or more AR/VR displays 312, one or more optional interior and/or exterior facing image sensors 314, one or more optional depth sensors 316, a memory 320, and one or more communication buses 304 for interconnecting these and various other components.

In some implementations, the one or more communication buses 304 include circuitry that interconnects and controls communications between system components. In some implementations, the one or more I/O devices and sensors 306 include at least one of an inertial measurement unit (IMU), an accelerometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, and/or the like.

In some implementations, the one or more AR/VR displays 312 are configured to present the AR/VR experience to the user. In some implementations, the one or more AR/VR displays 312 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electro-mechanical system (MEMS), and/or the like display types. In some implementations, the one or more AR/VR displays 312 correspond to diffractive, reflective, polarized, holographic, etc. waveguide displays. For example, the HMD 120 includes a single AR/VR display. In another example, the HMD 120 includes an AR/VR display for each eye of the user. In some implementations, the one or more AR/VR displays 312 are capable of presenting AR and VR content. In some implementations, the one or more AR/VR displays 312 are capable of presenting AR or VR content.

In some implementations, the one or more optional image sensors 314 are configured to obtain image data that corresponds to at least a portion of the face of the user that includes the eyes of the user. For example, the one or more optional image sensors 314 correspond to one or more RGB camera (e.g., with a complimentary metal-oxide-semiconductor (CMOS) image sensor or a charge-coupled device (CCD) image sensor), infrared (IR) image sensor, event-based camera, and/or the like.

In some implementations, the one or more optional depth sensors 316 are configured to obtain depth data that corresponds to at least a portion of the face of the user and to synthesize a depth/mesh map of the face of the user, where the mesh map characterizes the facial topography of the user. For example, the one or more optional depth sensors 316 correspond to a structured light device, a time-of-flight device, and/or the like.

The memory 320 includes high-speed random-access memory, such as DRAM, SRAM, DDR RAM, or other random-access solid-state memory devices. In some implementations, the memory 320 includes non-volatile memory, such as one or more magnetic disk storage devices, optical disk storage devices, flash memory devices, or other non-volatile solid-state storage devices. The memory 320 optionally includes one or more storage devices remotely located from the one or more processing units 302. The memory 320 comprises a non-transitory computer readable storage medium. In some implementations, the memory 320 or the non-transitory computer readable storage medium of the memory 320 stores the following programs, modules and data structures, or a subset thereof including an optional operating system 330, an AR/VR presentation module 340, and a user data store 360.

In some implementations, the user data store 360 stores one or more user profiles each including personal, demographic, biometric, etc. information for a respective user. For example, the user data store 360 includes a respective user profile that includes at least some of the following for an associated user: name, date of birth, mobile phone number, work phone number, home phone number, personal email address, work email address, average resting heartbeat, IPD measurement, head circumference, and/or the like.

The operating system 330 includes procedures for handling various basic system services and for performing hardware dependent tasks. In some implementations, the AR/VR presentation module 340 is configured to present AR/VR content to the user via the one or more AR/VR displays 312. To that end, in various implementations, the AR/VR presentation module 340 includes a data obtaining unit 342, an AR/VR presenting unit 344, an optional IPD determining unit 346, an AR/VR calibration unit 348, and a data transmitting unit 350.

In some implementations, the data obtaining unit 342 is configured to obtain data (e.g., presentation data, user interaction data, sensor data, location data, etc.) from at least one of the controller 110 and the calibration device 130. To that end, in various implementations, the data obtaining unit 342 includes instructions and/or logic therefor, and heuristics and metadata therefor.

In some implementations, the AR/VR presenting unit 344 is configured to present AR/VR content via the one or more AR/VR displays 312. To that end, in various implementations, the AR/VR presenting unit 344 includes instructions and/or logic therefor, and heuristics and metadata therefor.

In some implementations, the optional IPD determining unit 346 is configured to determine the IPD measurement for the user of the HMD 120 based on the position of the user's eyes in image data obtained by the one or more optional image sensor 314 and a depth measurement from the HMD 120 to a point on the user's face determined based on the mesh map synthesized by the one or more optional depth sensors 316. To that end, in various implementations, the IPD determining unit 346 includes instructions and/or logic therefor, and heuristics and metadata therefor.

In some implementations, the AR/VR calibration unit 348 is configured to calibrate the HMD 120 by setting one or more presentation parameters (e.g., software and/or hardware parameters) of the HMD 120 based on the determined IPD measurement in order to tailor one or more AR/VR displays 312 of the HMD 120 to a field-of-view of the user. To that end, in various implementations, the AR/VR calibration unit 348 includes instructions and/or logic therefor, and heuristics and metadata therefor.

In some implementations, the data transmitting unit 350 is configured to transmit data (e.g., presentation data, location data, user interaction data, etc.) to at least one of the controller 110 and the calibration device 130. To that end, in various implementations, the data transmitting unit 350 includes instructions and/or logic therefor, and heuristics and metadata therefor.

Although the data obtaining unit 342, the AR/VR presenting unit 344, the optional IPD determining unit 346, the AR/VR calibration unit 348, and the data transmitting unit 350 are shown as residing on a single device (e.g., the HMD 120), it should be understood that in other implementations, any combination of the data obtaining unit 342, the AR/VR presenting unit 344, the optional IPD determining unit 346, the AR/VR calibration unit 348, and the data transmitting unit 350 may be located in separate computing devices.

Moreover, FIG. 3 is intended more as a functional description of the various features which are present in a particular embodiment as opposed to a structural schematic of the implementations described herein. As recognized by those of ordinary skill in the art, items shown separately could be combined and some items could be separated. For example, some functional modules shown separately in FIG. 3 could be implemented in a single module and the various functions of single functional blocks could be implemented by one or more functional blocks in various implementations. The actual number of modules and the division of particular functions and how features are allocated among them will vary from one embodiment to another and, in some implementations, depends in part on the particular combination of hardware, software, and/or firmware chosen for a particular embodiment.

Figure 4:
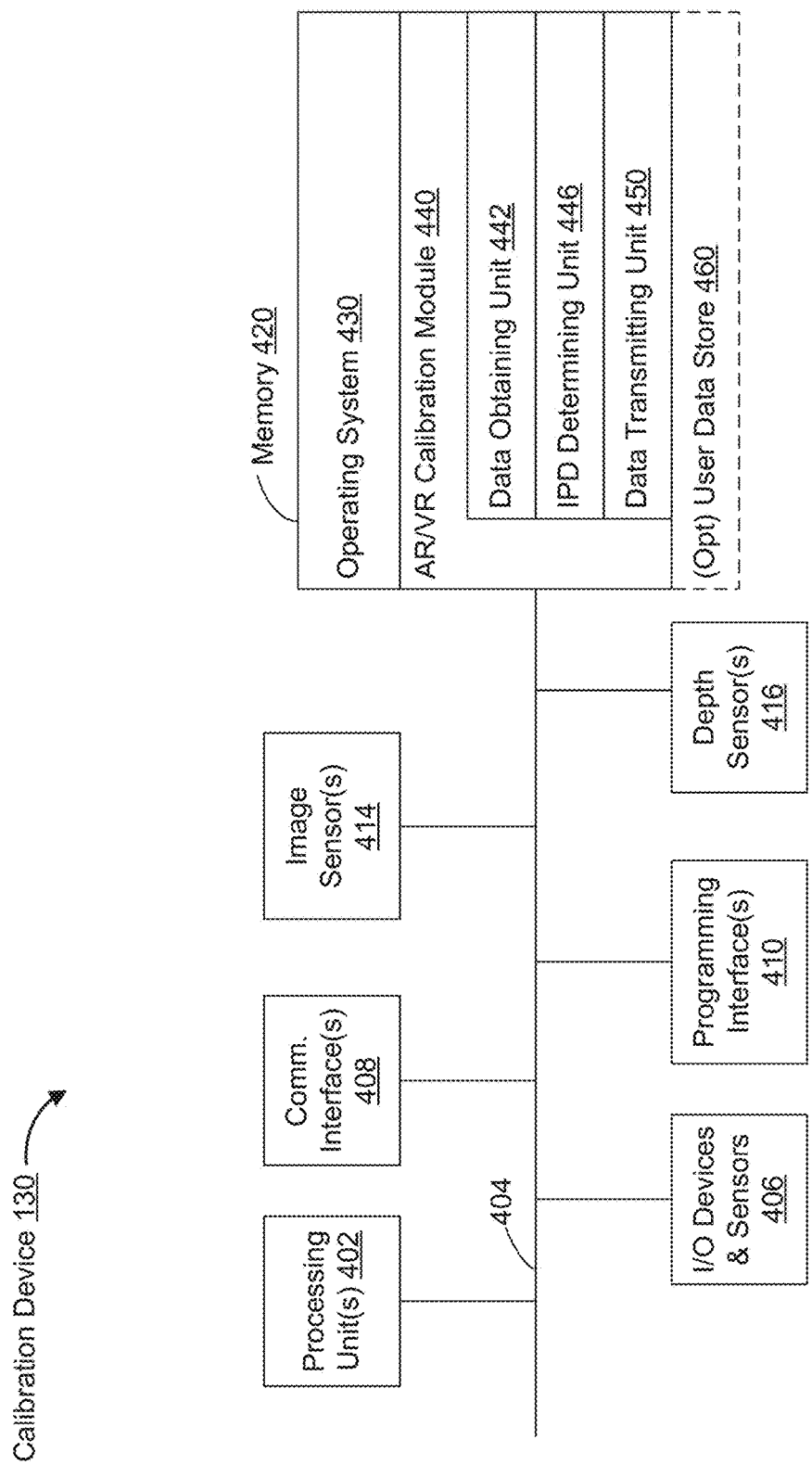
FIG. 4 is a block diagram of an example calibration device in accordance with some implementations.

FIG. 4 is a block diagram of an example of the calibration device 130 in accordance with some implementations. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the calibration device 130 includes one or more processing units 402 (e.g., microprocessors, ASICs, FPGAs, GPUs, CPUs, processing cores, and/or the like), one or more input/output (I/O) devices and sensors 406, one or more communication interfaces 408 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, and/or the like type interface), one or more programming (e.g., I/O) interfaces 410, one or more front and/or rear facing image sensors 414, one or more depth sensors 416, a memory 420, and one or more communication buses 404 for interconnecting these and various other components.

In some implementations, the one or more communication buses 404 include circuitry that interconnects and controls communications between system components. In some implementations, the one or more I/O devices and sensors 406 include at least one of an IMU, an accelerometer, a gyroscope, a thermometer, one or more physiological sensors (e.g., blood pressure monitor, heart rate monitor, blood oxygen sensor, blood glucose sensor, etc.), a keyboard, a mouse, a touchpad, a joystick, one or more microphones, one or more speakers, one or more image sensors, one or more displays, and/or the like.

In some implementations, the one or more image sensors 414 are configured to obtain image data that corresponds to at least a portion of the face of the user that includes the eyes of the user. For example, the one or more optional image sensors 414 correspond to one or more RGB camera (e.g., with a CMOS or CCD image sensor), IR camera, event-based camera, and/or the like.

In some implementations, the one or more depth sensors 416 are configured to obtain depth data that corresponds to at least a portion of the face of the user and to synthesize a depth/mesh map of the face of the user, where the mesh map characterizes the facial topography of the user. For example, the one or more optional depth sensors 416 correspond to a structured light device, a time-of-flight device, and/or the like.

The memory 420 includes high-speed random-access memory, such as DRAM, SRAM, DDR RAM, or other random-access solid-state memory devices. In some implementations, the memory 420 includes non-volatile memory, such as one or more magnetic disk storage devices, optical disk storage devices, flash memory devices, or other non-volatile solid-state storage devices. The memory 420 optionally includes one or more storage devices remotely located from the one or more processing units 402. The memory 420 comprises a non-transitory computer readable storage medium. In some implementations, the memory 420 or the non-transitory computer readable storage medium of the memory 420 stores the following programs, modules and data structures, or a subset thereof including an optional operating system 430, an AR/VR calibration module 440, and an optional user data store 460.

In some implementations, the optional user data store 460 stores one or more user profiles each including personal, demographic, biometric, etc. information for a respective user. For example, the user data store 460 includes a respective user profile that includes at least some of the following for an associated user: name, date of birth, mobile phone number, work phone number, home phone number, personal email address, work email address, average resting heartbeat, IPD measurement, head circumference, and/or the like.

The operating system 430 includes procedures for handling various basic system services and for performing hardware dependent tasks. In some implementations, the AR/VR calibration module 440 is configured to calibrate the HMD 120 by setting one or more presentation parameters (e.g., software and/or hardware parameters) of the HMD 120 based on the determined IPD measurement in order to tailor one or more AR/VR displays 312 of the HMD 120 to a field-of-view of the user. To that end, in various implementations, the AR/VR calibration module 440 includes a data obtaining unit 442, an IPD determining unit 446, and a data transmitting unit 450.

In some implementations, the data obtaining unit 442 is configured to obtain data (e.g., presentation data, user interaction data, sensor data, location data, etc.) from at least one of the controller 110 and the HMD 120. To that end, in various implementations, the data obtaining unit 442 includes instructions and/or logic therefor, and heuristics and metadata therefor.

In some implementations, the IPD determining unit 446 is configured to determine the IPD measurement for the user of the HMD 120 based on the position of the user's eyes in image data obtained by the one or more image sensor 414 and a depth measurement from the HMD 120 to a point on the user's face determined based on the mesh map synthesized by the one or more depth sensors 416. To that end, in various implementations, the IPD determining unit 446 includes instructions and/or logic therefor, and heuristics and metadata therefor.

In some implementations, the data transmitting unit 450 is configured to transmit data (e.g., presentation data, location data, user interaction data, etc.) to at least one of the controller 110 and the HMD 120. To that end, in various implementations, the data transmitting unit 450 includes instructions and/or logic therefor, and heuristics and metadata therefor.

Although the data obtaining unit 442, the IPD determining unit 446, and the data transmitting unit 450 are shown as residing on a single device (e.g., the calibration device 130), it should be understood that in other implementations, any combination of the data obtaining unit 442, the IPD determining unit 446, and the data transmitting unit 450 may be located in separate computing devices.

Moreover, FIG. 4 is intended more as a functional description of the various features which are present in a particular embodiment as opposed to a structural schematic of the implementations described herein. As recognized by those of ordinary skill in the art, items shown separately could be combined and some items could be separated. For example, some functional modules shown separately in FIG. 4 could be implemented in a single module and the various functions of single functional blocks could be implemented by one or more functional blocks in various implementations. The actual number of modules and the division of particular functions and how features are allocated among them will vary from one embodiment to another and, in some implementations, depends in part on the particular combination of hardware, software, and/or firmware chosen for a particular embodiment.

FIG. 5A illustrates example image data 500 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the device (e.g., the calibration device 130 in FIGS. 1 and 4) obtains image data 500 (e.g., raw image data or pre-processed image data such as an RGB or YCbCr image) of a scene in a 2D image space from the image sensor. For example, the calibration device 130 captures a "selfie" of the user using one or more front facing image sensors 414 of the calibration device 130.

In some implementations, the device identifies a face 505 (or a region thereof) within the image data 500. For example, the device identifies the face 505 based on known facial recognition or computer vision algorithms or techniques. In some implementations, the device identifies positions 510*a* and 510*b* of the eyes. For example, the positions 510*a* and 510*b* of the eyes correspond to pixel coordinates in the 2D image space. In another example, the positions 510*a* and 510*b* of the eyes correspond to absolute or relative coordinates when the location of the device and a mapping of the scene are known. In some implementations, the device determines a distance measurement 515 between the eyes based on the positions 510*a* and 510*b* of the eyes within the 2D image space.

Figure 5B:
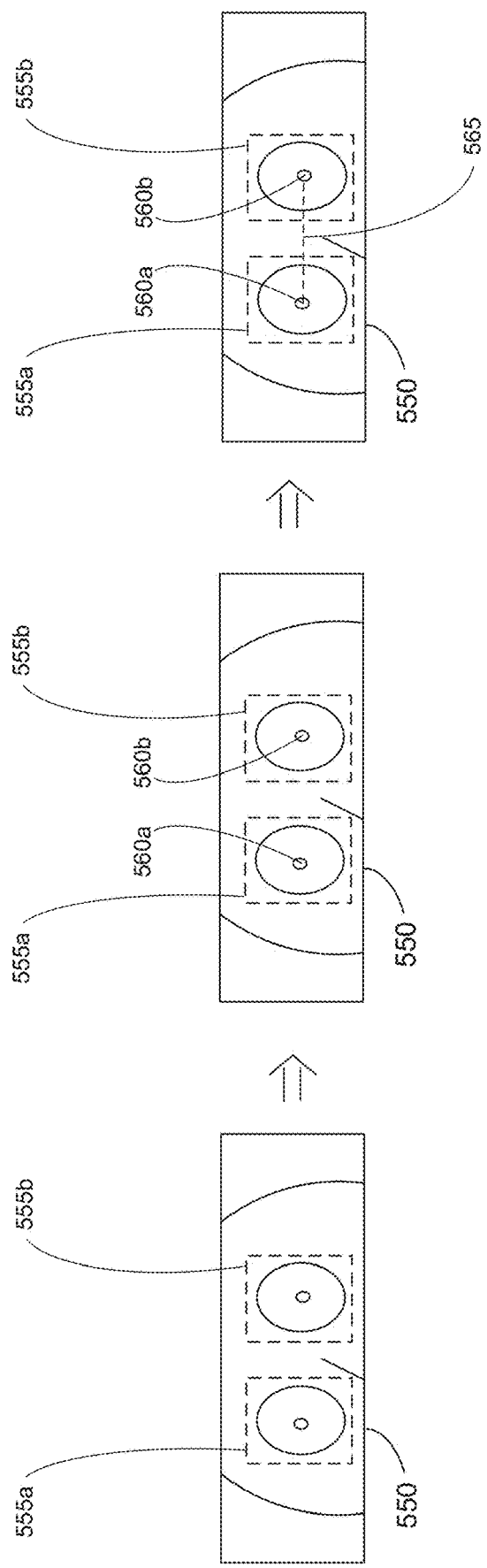

FIG. 5B illustrates example image data 550 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the device (e.g., the HMD device 120 in FIGS. 1 and 3) obtains image data 550 (e.g., raw image data or pre-processed image data such as an RGB or YCbCr image) of a scene in a 2D image space from the image sensor. For example, the HMD 120 captures an image of a strip of the user's face that includes the eyes using one or more interior facing image sensors 314 of the HMD 120. In some implementations, the image data 550 corresponds to composite image data generated image data from two or more interior facing image sensors of the HMD 120. In some implementations, the image data 550 corresponds to image data from a single interior facing image sensor of the HMD 120.

In some implementations, the device identifies eyes 555a and 555b (or a region(s) thereof) within the image data 550. For example, the device identifies the eyes 555a and 555b based on known eye recognition or computer vision algorithms or techniques. In some implementations, the device identifies positions 560a and 560b of the eyes. For example, the positions 560a and 560b of the eyes correspond to pixel coordinates in the 2D image space. In some implementations, the device determines a distance measurement 565 between the eyes based on the positions 560a and 560b of the eyes within the 2D image space.

Figure 6:
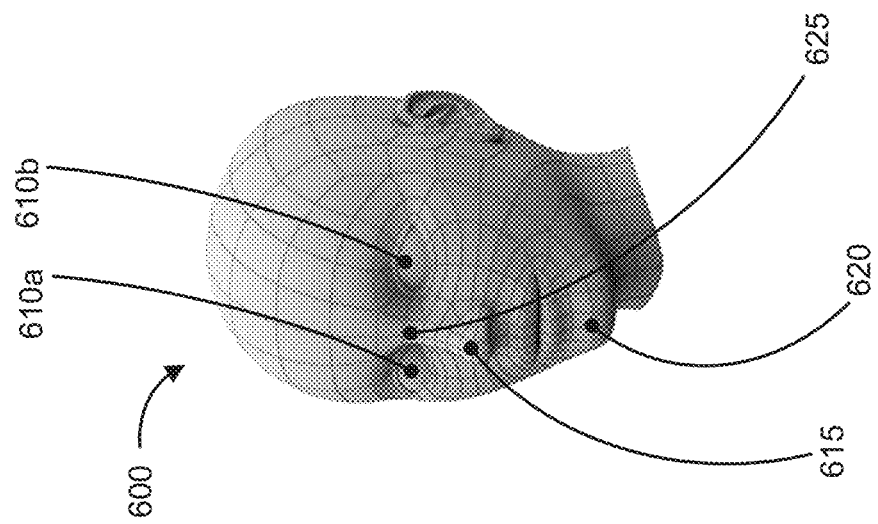
FIG. 6 illustrates example depth data in accordance with some implementations.
Figure 6:
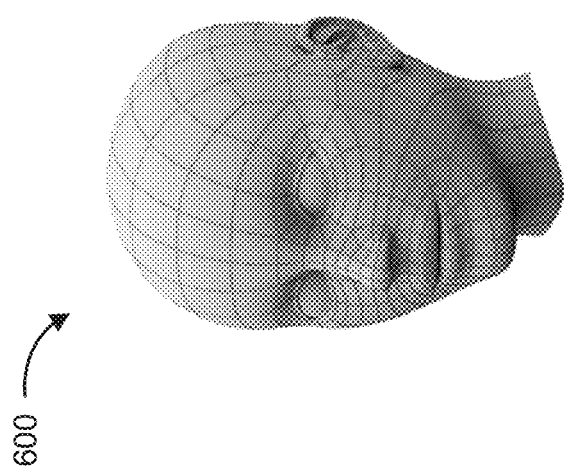

FIG. 6 illustrates example depth data in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the device (e.g., the HMD device 120 or the calibration device 130 in FIGS. 1 and 3-4) obtains depth data for at least a portion of a face of a user from a depth sensor. For example, with reference to FIG. 3, the HMD 120 obtains depth data for at least a strip of the face of the user that includes the eyes using the one or more depth sensors 316. In another example, with reference to FIG. 4, the calibration device 130 obtains depth data for the face of the user using the one or more depth sensors 416. In some implementations, the device synthesizes a depth/mesh map 600 of at least a portion of the face of the user based on the depth data from the one or more depth sensors. For example, the depth/mesh map 600 provides a characterization of facial topography of the user.

In some implementations, the device identifies at least one reference point within the depth/mesh map 600 and determines a depth measurement based on a distance from the device to the at least reference point. As one example, the device identifies the eyes 610a and/or 610b as reference points and determines a distance from one or both of the eyes 610a and 610b to the device as the depth measurement. In another example, the device identifies the tip of the nose 615 as a reference point and determines a distance from the tip of the nose 615 to the device as the depth measurement. In yet other example, the device identifies the chin 620 as a reference point and determines a distance from the chin 620 to the device as the depth measurement. In yet other example, the device identifies the bridge of the nose 625 as a reference point and determines a distance from the bridge of the nose 625 to the device as the depth measurement.

Figure 7:
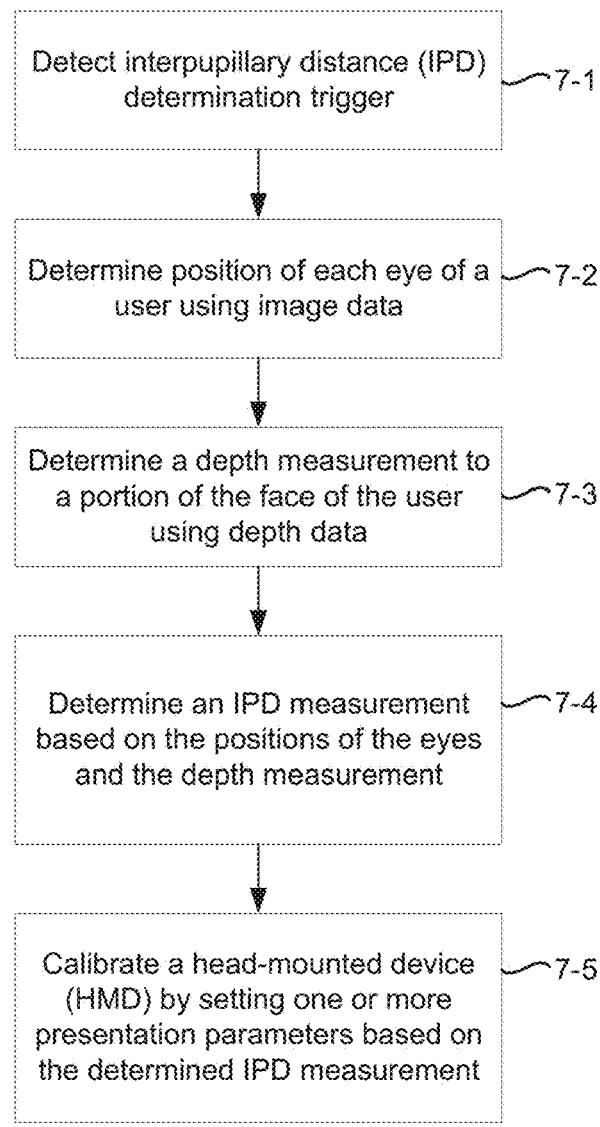
FIG. 7 is a flowchart representation of a method of determining an interpupillary distance (IPD) based on image and depth data in accordance with some implementations.

FIG. 7 is a flowchart representation of a method 700 of determining an interpupillary distance (IPD) based on image and depth data in accordance with some implementations. In various implementations, the method 700 is performed by a device (e.g., the HMD 120 or the calibration device 130 in FIGS. 1 and 3-4) with one or more processors, non-transitory memory, an image sensor, and a depth sensor. In some implementations, the method 700 is performed by processing logic, including hardware, firmware, software, or a combination thereof. In some implementations, the method 700 is performed by a processor executing code stored in a non-transitory computer-readable medium (e.g., a memory). Briefly, in some circumstances, the method 700 includes: determining a position of each eye of a user using image data; determining a depth measurement to a portion of the face of the user using a depth/mesh map; determining an interpupillary distance (IPD) measurement based on the positions of the eyes and the depth measurement; and calibrating a head-mounted device (HMD) by setting one or more presentation parameters based on the IPD measurement.

In some implementations, the device corresponds to calibration device 130 in FIG. 4 used to calibrate the HMD 120 in FIG. 3 (e.g., by setting one or more presentation parameters associated with the one or more AR/VR displays 312 of the HMD 120). In some implementations, the device corresponds to the HMD 120 in FIG. 2 that includes the one or more AR/VR displays 312.

As represented by block 7-1, the method 700 includes detecting an IPD determination trigger. For example, with reference to FIG. 3, the HMD 120 or a component thereof (e.g., the IPD determining unit 346) detects a trigger that corresponds to initiating the method 700. For example, with reference to FIG. 4, the calibration device 130 or a component thereof (e.g., the IPD determining unit 446) detects a trigger that corresponds to initiating the method 700. In one example, the trigger corresponds to a user profile population process (e.g., an account setup workflow) when initializing or setting up the device. In another example, the trigger corresponds to a request to calibrate the IPD measurement.

As represented by block 7-2, the method 700 includes determining a position of each eye of a user using image data. In some implementations, when the image data at least includes a portrait of the user, the device detects a face of the user within the image data and, subsequently, determines the position of the user's eyes. In some implementations, when the image data includes a tract of the user's face with the user's eyes and another reference point such as the user's nose, chin, etc., the device detects the eyes within the image data and, subsequently, determines the position of the user's eyes.

As one example, with reference to FIG. 3, the HMD 120 or a component thereof (e.g., the IPD determining unit 346) obtains image data from the image sensors 314 and determines a position of each eye in the image data. For example, with reference to FIGS. 3 and 5B, the HMD 120 captures an image of a strip of the user's face that includes the eyes using one or more interior facing image sensors 314 of the HMD 120. Continuing with this example, the HMD 120 identifies eyes the 555a and 555b (or a region thereof) within the image data 550.

As another example, with reference to FIG. 4, the calibration device 130 or a component thereof (e.g., the IPD determining unit 446) obtains image data from the image sensors 414 and determines a position of each eye in the image data. For example, with reference to FIGS. 4 and 5A, the calibration device 130 captures a "selfie" of the user using one or more front facing image sensors 414 of the calibration device 130. Continuing with this example, the calibration device 130 identifies the face 505 (or a region thereof) within the image data 500.

As represented by block 7-3, the method 700 includes determining a depth measurement to a portion of the face of the user using depth data. For example, the depth measurement corresponds to a distance from the device (or the depth sensor thereof) to a reference point on the user's face such as a centroid of the nose, bridge of the nose, tip of the nose, centroid of the chin, tip of the chin, forehead, or the like. In another example, the depth measurement corresponds to a distance from the device (or the depth sensor thereof) to one of the user's eyes, a function of the positions of both of the user's eyes (e.g., a depth measurement to a center point between the eyes, or the mean depth based on the depth measurement to each of the user's eyes), or the like. In yet another example, the depth measurement corresponds to a distance from the device (or the depth sensor thereof) to a reference point not on the user's face such as the neck, shoulder(s), mid-point between shoulders, chest, or the like.

In one example, with reference to FIG. 3, the HMD 120 or a component thereof (e.g., the IPD determining unit 346) obtains the depth data for at least a strip of the face of the user that includes the eyes using the one or more depth sensors 316. For example, with reference to FIGS. 3 and 6, the HMD 120 synthesizes the depth/mesh map 600 of at least a portion of the face of the user based on the depth data from the one or more depth sensors 316. Continuing with this example, the HMD 120 identifies at least one reference point within the depth/mesh map 600 and determines a depth measurement based on a distance from the device to the at least reference point.

As another example, with reference to FIG. 4, the calibration device 130 or a component thereof (e.g., the IPD determining unit 446) obtains the depth data for at least a strip of the face of the user that includes the eyes using the one or more depth sensors 416. For example, with reference to FIGS. 4 and 6, the calibration device 130 synthesizes the depth/mesh map 600 of at least a portion of the face of the user based on the depth data from the one or more depth sensors 416. Continuing with this example, the calibration device 130 identifies at least one reference point within the depth/mesh map 600 and determines a depth measurement based on a distance from the device to the at least reference point.

In some implementations, the device performs blocks 7-2 and 7-3 in sequence as shown in FIG. 7. In some implementations, the device performs blocks 7-2 and 7-3 in parallel. In some implementations, the positions of the eyes are determined in block 7-2 using image data and/or depth data. In some implementations, the depth measurement is determined in block 7-3 using image data and/or depth data.

As represented by block 7-4, the method 700 includes determining an IPD measurement based on the positions of the eyes and the depth measurement. As such, in some implementations, the IPD measurement is determined based on a function of the image data and the depth data. In some implementations, the IPD measurement includes at least one of the distance from the device to a portion of the face of the user, a tilt angle relative to one or more reference points (e.g., the tip of nose, bridge of nose, centroid of nose, tip of chin, eye(s), etc.), and a pitch angle relative to the one or more reference points (e.g., tip of nose, bridge of nose, centroid of nose, tip of chin, eye(s), etc.). For example, the IPD measurement corresponds to a center-to-center Euclidean distance between the corneas, pupils, retinae, optic nerves, fovea centralae, or the like of the eyes. In another example, the IPD measurement also indicates tilt and/or pitch of the eye-to-eye measurement in 3D space. In some implementations, when the device determines the IPD measurement using both the position of the eyes in the 2D image space and the depth measurement, the IPD measurement is more accurate than when determined using one of the aforementioned measurements.

As one example, with reference to FIG. 3, the HMD 120 or a component thereof (e.g., the IPD determining unit 346) determines an IPD measurement for a particular user based on the positions of the eyes from block 7-2 and the depth measurement from block 7-3. As another example, with reference to FIG. 4, the calibration device 130 or a component thereof (e.g., the IPD determining unit 446) determines an IPD measurement for a particular user based on the positions of the eyes from block 7-2 and the depth measurement from block 7-3.

As represented by block 7-5, the method 700 includes calibrating an HMD provided to deliver AR/VR content by setting one or more presentation parameters of the HMD based on the determined IPD measurement in order to tailor one or more AR/VR displays of the HMD to a field-of-view of the user. In some implementations, the HMD tailors the one or more AR/VR displays to the user by adjusting how the one or more AR/VR displays render AR/VR content based on IPD measurement. In some implementations, the HMD tailors the one or more AR/VR displays to the user by adjusting one or more lens positions, one or more lens warp values, one or more displays positions, rendering positions, and/or the like based on the IPD measurement. In some implementations, the device corresponds to a self-calibrating HMD. As an example, the device corresponds to an auxiliary device (e.g., as a mobile phone, tablet, webcam, set-top box, over-the-top device, gaming console, kiosk, etc.) that assists in calibrating the HMD.

For example, with reference to FIG. 3, the HMD 120 or a component thereof (e.g., the AR/VR calibration unit 348) sets the one or more presentation parameters of the HMD 120 based on the IPD measurement from block 7-4. As another example, with reference to FIGS. 3-4, the calibration device 130 or a component thereof (e.g., the data transmitting unit 450) transmits the IPD measurement from block 7-4 to the HMD 120, and, in response to obtaining the IPD measurement, the HMD 120 or a component thereof (e.g., the AR/VR calibration unit 348) sets the one or more presentation parameters of the HMD 120 based on the IPD measurement from the calibration device 130.

In some implementations, setting one or more presentation parameters of the HMD based on the IPD measurement includes adjusting a focus point of the AR/VR content rendered by the one or more AR/VR displays based on the IPD measurement. In some implementations, setting one or more presentation parameters of the HMD based on the IPD measurement includes adjusting a presentation position of the AR/VR content rendered by the one or more AR/VR displays based on the IPD measurement. In some implementations, setting one or more presentation parameters of the HMD based on the IPD measurement includes adjusting a warping parameter of the AR/VR content rendered by the one or more AR/VR displays based on the IPD measurement.

In some implementations, setting one or more presentation parameters of the HMD based on the IPD measurement includes adjusting a position of at least one of the one or more AR/VR displays based on the IPD measurement. In some implementations, setting one or more presentation parameters of the HMD based on the IPD measurement includes adjusting at least one lens parameter associated with the one or more AR/VR displays based on the IPD measurement. In some implementations, the at least one lens parameter corresponds to one of a lens warping parameter, a focal length parameter, and an aperture parameter.

In some implementations, the device also stores the IPD measurement in a user profile associated with the user, wherein the user profile at least includes biometric information associated with the user. In some implementations, the device also updates the IPD measurement based on an adjustment input from the user (e.g., a manual fine-tuning input).

Figure 8:
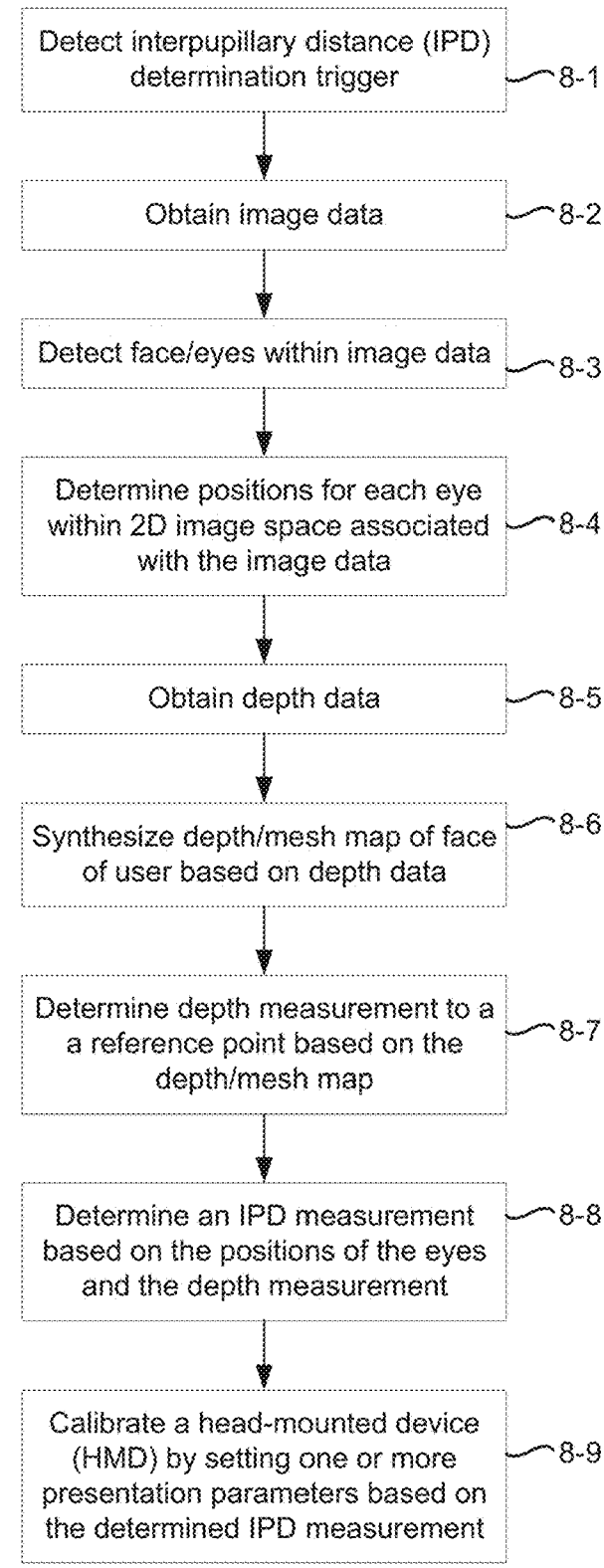
FIG. 8 is a flowchart representation of another method of determining an IPD based on image and depth data in accordance with some implementations.

FIG. 8 is a flowchart representation of a method 800 of determining an IPD based on image and depth data in accordance with some implementations. In various implementations, the method 800 is performed by a device with one or more processors, non-transitory memory, an image sensor, and a depth sensor (e.g., the HMD 120 or the calibration device 130 in FIGS. 1 and 3-4). In some implementations, the method 800 is performed by processing logic, including hardware, firmware, software, or a combination thereof. In some implementations, the method 800 is performed by a processor executing code stored in a non-transitory computer-readable medium (e.g., a memory).

In some implementations, the device corresponds to calibration device 130 in FIG. 4 used to calibrate the HMD 120 in FIG. 3 (e.g., by setting one or more presentation parameters associated with the one or more AR/VR displays 312 of the HMD 120). In some implementations, the device corresponds to the HMD 120 in FIG. 3 that includes the one or more AR/VR displays 312.

In some implementations, as represented by block 8-1, the method 800 includes detecting an IPD determination trigger. For example, in some implementations, the block 8-1 is similar to and adapted from block 7-1 described above with reference to FIG. 7. Thus, block 8-1 will not be described again for the sake of brevity.

As represented by block 8-2, the method 800 includes obtaining image data. As represented by block 8-3, the method 800 includes detecting a face and/or eyes of a user (or region(s) thereof) within the image data. As one example, with reference to FIG. 3, the HMD 120 or a component thereof (e.g., the IPD determining unit 346) obtains image data from the image sensors 314 and determines a position of each eye in the image data. For example, with reference to FIGS. 3 and 5B, the HMD 120 captures an image of a strip of the user's face that includes the eyes using one or more interior facing image sensors 314 of the HMD 120. Continuing with this example, the HMD 120 identifies eyes 555a and 555b (or a region thereof) within the image data 550.

As another example, with reference to FIG. 4, the calibration device 130 or a component thereof (e.g., the IPD determining unit 446) obtains image data from the image sensors 414 and determines a position of each eye in the image data. For example, with reference to FIGS. 4 and 5A, the calibration device 130 captures a "selfie" of the user using one or more front facing image sensors 414 of the calibration device 130.

As represented by block 8-4, the method 800 includes determining positions for each eye with 2D image space associated with the image data. For example, in some implementations, the block 8-4 is similar to and adapted from block 7-2 described above with reference to FIG. 7. Thus, block 8-4 will not be described again for the sake of brevity. In some implementations, the positions of the eyes are determined in block 8-4 using image data and/or depth data.

As represented by block 8-5, the method 800 includes obtaining depth data. As represented by block 8-6, the method 800 includes synthesizing a depth/mesh map of at least a portion of the face of the user based on the depth data.

In one example, with reference to FIG. 3, the HMD 120 or a component thereof (e.g., the IPD determining unit 346) obtains depth data for at least a strip of the face of the user that includes the eyes using the one or more depth sensors 316. For example, with reference to FIGS. 3 and 6, the HMD 120 synthesizes the depth/mesh map 600 of at least a portion of the face of the user based on the depth data from the one or more depth sensors 316. Continuing with this example, the HMD 120 identifies at least one reference point within the depth/mesh map 600 and determines a depth measurement based on a distance from the device to the at least reference point.

As another example, with reference to FIG. 4, the calibration device 130 or a component thereof (e.g., the IPD determining unit 446) obtains depth data for at least a strip of the face of the user that includes the eyes using the one or more depth sensors 416. For example, with reference to FIGS. 4 and 6, the calibration device 130 synthesizes the depth/mesh map 600 of at least a portion of the face of the user based on the depth data from the one or more depth sensors 416. Continuing with this example, the calibration device 130 identifies at least one reference point within the depth/mesh map 600 and determines a depth measurement based on a distance from the device to the at least reference point.

As represented by block 8-7, the method 800 includes determining a depth measurement to a reference point based on the depth/mesh map synthesized in block 8-6. For example, in some implementations, the block 8-7 is similar to and adapted from block 7-3 described above with reference to FIG. 7. Thus, block 8-7 will not be described again for the sake of brevity. In some implementations, the depth measurement is determined in block 8-7 using image data and/or depth data.

In some implementations, the device performs the set of blocks 8-2 through 8-4 associated with determining the positions of the eyes and the set of blocks 8-5 through 8-7 associated with determining the depth measurement in sequence as shown in FIG. 8. In some implementations, the device performs the set of blocks 8-2 through 8-4 associated with determining the positions of the eyes and the set of blocks 8-5 through 8-7 associated with determining the depth measurement in parallel.

As represented by block 8-8, the method 800 includes determining an IPD measurement based on the positions of the eyes and the depth measurement. As such, in some implementations, the IPD measurement is determined based on a function of the image data and the depth data. For example, in some implementations, the block 8-8 is similar to and adapted from block 7-4 described above with reference to FIG. 7. Thus, block 8-8 will not be described again for the sake of brevity.

As represented by block 8-9, the method 800 includes calibrating an HMD provided to deliver AR/VR content by setting one or more presentation parameters of the HMD based on the determined IPD measurement in order to tailor one or more AR/VR displays of the HMD to a field-of-view of the user. For example, in some implementations, the block 8-9 is similar to and adapted from block 7-5 described above with reference to FIG. 7. Thus, block 8-9 will not be described again for the sake of brevity.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first," "second," etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular embodiments only and is not intended to be limiting of the claims. As used in the description of the embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
    at a device with one or more processors, non-transitory memory, an image sensor, and a depth sensor:
        determining an interpupillary distance (IPD) measurement for a user based on a function of depth data obtained by the depth sensor and image data obtained by the image sensor;
        detecting a trigger to adjust an assembled head-mounted device (HMD) that has been built to fit users with different physiological measurements; and
        adjusting a combination of a focus point, a presentation point and a warping parameter associated with the assembled HMD based on the IPD measurement in order to tailor one or more AR/VR displays of the HMD to a field-of-view of the user.

2. The method of claim 1 further comprising:
    determining a position of each eye of the user within the image data obtained by the image sensor; and
    determining a depth measurement associated with the depth data obtained by the depth sensor, the depth measurement characterizing a distance from the device to a portion of the face of the user,
    wherein the IPD measurement is determined based on a function of the positions of the eyes and the depth measurement.

3. The method of claim 2 further comprising, obtaining depth data by the depth sensor, and synthesizing a mesh map of at least a portion of the face of the user based on the depth data, wherein the mesh map provides a characterization of facial topography of the user; and wherein the depth measurement is determined based on the mesh map.

4. The method of claim 2, wherein the portion of the face of the user associated with the depth measurement corresponds to at least one eye of the user.

5. The method of claim 1, wherein the IPD measurement includes at least one of the distance from the device to a portion of the face of the user, a tilt angle relative to one or more reference points, and a pitch angle relative to the one or more reference points.

6. The method of claim 1, wherein adjusting the focus point comprises adjusting a focus point of AR/VR content rendered by the one or more AR/VR displays based on the IPD measurement.

7. The method of claim 1, wherein includes adjusting the presentation position comprises adjusting a presentation position of AR/VR content rendered by the one or more AR/VR displays based on the IPD measurement.

8. The method of claim 1, wherein adjusting the warping parameter comprises adjusting a warping parameter of AR/VR content rendered by the one or more AR/VR displays based on the IPD measurement.

9. The method of claim 1, further comprising adjusting a position of at least one of the one or more AR/VR displays based on the IPD measurement.

10. The method of claim 1, further comprising adjusting at least one lens parameter associated with the one or more AR/VR displays based on the IPD measurement.

11. The method of claim 10, wherein the at least one lens parameter corresponds to one of a lens warping parameter, a focal length parameter, and an aperture parameter.

12. The method of claim 1 further comprising, storing the IPD measurement in a user profile associated with the user, wherein the user profile at least includes biometric information associated with the user.

13. The method of claim 1 further comprising, obtaining an adjustment input from the user, and updating the IPD measurement based on the adjustment input.

14. The method of claim 1, wherein at least one of the focus point, the presentation position and the warping parameter is a software parameter.

15. The method of claim 14, wherein adjusting the software parameter changes how the one or more AR/VR displays render AR/VR content without triggering a physical change in the HMD.

16. A device comprising:
    one or more processors;
    a non-transitory memory;
    an image sensor;
    a depth sensor; and
    one or more programs stored in the non-transitory memory, which, when executed by the one or more processors, cause the device to:

determine an interpupillary distance (IPD) measurement for a user based on a function of depth data obtained by the depth sensor and image data obtained by the image sensor;

detect a trigger to adjust an assembled head-mounted device (HMD) that has been built to fit users with different physiological measurements; and adjust a combination of a focus point, a presentation position and a lens warping parameter associated with the assembled HMD based on the IPD measurement in order to tailor one or more AR/VR displays of the HMD to a field-of-view of the user.

17. The device of claim 16, wherein the programs further cause the device to:

determine a position of each eye of the user within the image data obtained by the image sensor; and determine a depth measurement associated with the depth data obtained by the depth sensor, the depth measurement characterizing a distance from the device to a portion of the face of the user, wherein the IPD measurement is determined based on a function of the positions of the eyes and the depth measurement.

18. The device of claim 16, wherein the IPD measurement includes at least one of the distance from the device to a portion of the face of the user, a tilt angle relative to one or more reference points, and a pitch angle relative to the one or more reference points.

19. The device of claim 16, wherein adjusting the focus point includes adjusting a focus point of the AR/VR content rendered by the one or more AR/VR displays based on the IPD measurement.

20. The device of claim 16, wherein adjusting the presentation position includes adjusting a presentation position of the AR/VR content rendered by the one or more AR/VR displays based on the IPD measurement.

21. The device of claim 16, wherein the programs further cause the device to adjust at least one lens parameter associated with the one or more AR/VR displays based on the IPD measurement.

22. The device of claim 16, wherein at least one of the focus point, the presentation position and the warping parameter is a software parameter.

23. The device of claim 22, wherein adjusting the software parameter changes how the one or more AR/VR displays render AR/VR content without triggering a physical change in the HMD.

24. A non-transitory memory storing one or more programs, which, when executed by one or more processors of a device with an image sensor and a depth sensor, cause the device to:

determine an interpupillary distance (IPD) measurement for a user based on a function of depth data obtained by the depth sensor and image data obtained by the image sensor;

detect a trigger to adjust an assembled head-mounted device (HMD) that has been built to fit users with different physiological measurements; and adjust a combination of a focus point, a presentation position and a warping parameter associated with the assembled HMD based on the IPD measurement in order to tailor one or more AR/VR displays of the HMD to a field-of-view of the user.

25. The non-transitory memory of claim 24, wherein at least one of the focus point, the presentation position and the warping parameter is a software parameter.

26. The non-transitory memory of claim 25, wherein adjusting the software parameter changes how the one or more AR/VR displays render AR/VR content without triggering a physical change in the HMD.

* * * * *